US00PP24365P3

(12) United States Plant Patent
Schoone

(10) Patent No.: US PP24,365 P3
(45) Date of Patent: Apr. 1, 2014

(54) ***PHALAENOPSIS* ORCHID PLANT NAMED 'HUMMING BIRD'**

(50) Latin Name: ***Phalaenopsis* hybrid**
Varietal Denomination: Humming Bird

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 13/506,413

(22) Filed: Apr. 18, 2012

(65) Prior Publication Data

US 2012/0272420 P1 Oct. 25, 2012

Related U.S. Application Data

(60) Provisional application No. 61/478,809, filed on Apr. 25, 2011.

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named 'Humming Bird' particularly characterized by flowers which are bronzed (yellow/green covered with red/purple stripes and spots), with a purple labellum with some yellow and a white column; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Humming Bird'.

CROSS-REFERENCE TO RELATED APPLICATIONS

This application claims priority to U.S. Provisional Application No. 61/478,809, filed Apr. 25, 2011 and Netherlands Plant Breeders' Rights Application No. OPS789, filed Apr. 27, 2011. The disclosure of both prior applications are hereby incorporated by reference in their entirety.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Humming Bird'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Humming Bird' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Humming Bird' originated from a cross made by the inventor in 1998 in Strengweg, Heemskerk, The Netherlands. The female or seed parent is the *Phalaenopsis* cultivar designated 'Sara Gold', unpatented. The male or pollen parent is the *Phalaenopsis* cultivar designated 'Nobelstar', unpatented. The new *Phalaenopsis* 'Humming Bird' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in November, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Humming Bird', which in combination distinguish this *Phalaenopsis* as a new, and distinct cultivar:

1. flowers which are bronzed (yellow/green covered with red/purple stripes and spots), with a purple labellum with some yellow;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Humming Bird', the female parent 'Sara Gold' has yellow flowers with red/brown/purple marks and they are about 6 cm in size, the male parent 'Nobelstar' has yellow/violet colored flowers and they are about 6 cm in size, whereas the flowers of 'Humming Bird' are bronzed and are about 6 cm in size.

Presently, there is no commercial cultivar to which 'Humming Bird' can be meaningfully compared.

BRIEF DESCRIPTION OF THE PHOTOGRAPHS

The accompanying photographs illustrate the overall appearance of the new *Phalaenopsis* 'Humming Bird' showing the colors as true as is reasonably possible with colored reproductions of this type. Colors in the photographs may differ slightly from the color values cited in the detailed botanical description, which accurately describe the color of 'Humming Bird'.

DETAILED BOTANICAL DESCRIPTION

Figure 1:
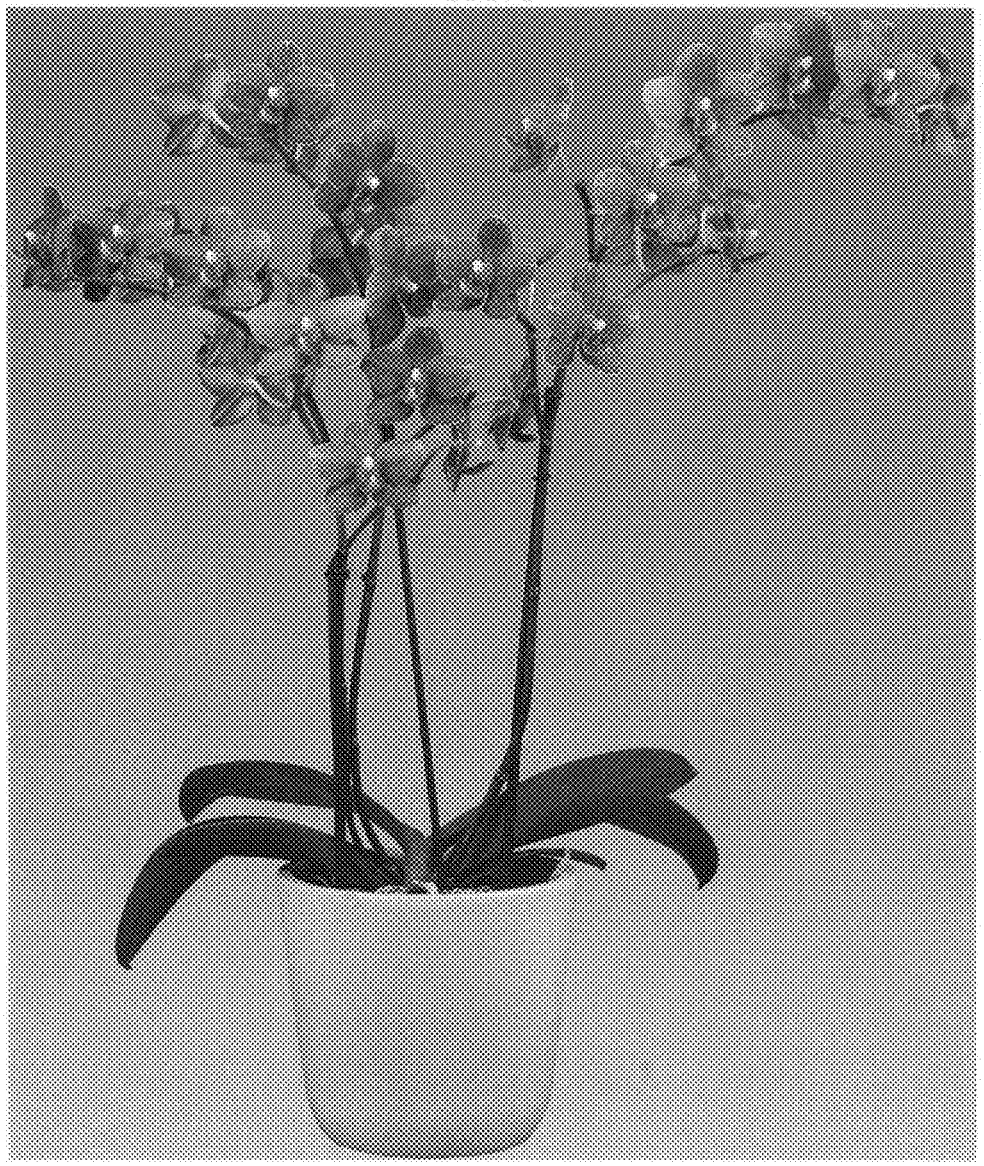
FIG. 1 shows a side view perspective of a typical flowering plant of 'Humming Bird' in a 12 cm pot, at 16 months of age.

The new *Phalaenopsis* cultivar 'Humming Bird' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Humming Bird' as grown in a greenhouse in Strengweg, Heemskerk, The Netherlands, under conditions which closely approximate those generally used in commercial practice. Initially, the ideal temperature to grow plants of 'Humming Bird' is 27° C. during the day and at night. Then, during the flowering phase of 'Humming Bird', the ideal growing temperature is 20-22° C. during the day and 18° C. at night. Light levels for growing 'Humming Bird' are a minimum of 5,000 lux and a maximum of 10,000 lux. A balanced fertilizer with level of 200 ppm N, 87 ppm P, 168 ppm K is applied. Duration of growth of 'Humming Bird' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Humming Bird' plants described is 12 months after potting.

Classification:

*Botanical.*—*Phalaenopsis* hybrid.

Parentage:

*Female or seed parent.*—*Phalaenopsis* cultivar designated 'Sara Gold', unpatented.

*Male or pollen parent.*—*Phalaenopsis* cultivar designated 'Nobelstar', unpatented.

Propagation:

*Type.*—Tissue culture.

*Rooting habit and description.*—Fleshy; approximately 5 mm-7 mm wide and greyed-green/green in color (combination of RHS 156D, RHS 128D, and RHS 137B); freely branching. It takes 12 weeks for plants growing in tissue culture to initiate roots.

Plant:

*Size at maturity.*—Height: about 57 cm. Spread: about 38 cm.

*Growth habit.*—Standard; green leaves (RHS 137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 17 to 20 cm.

*Mature leaf width.*—About 7 to 9 cm.

*Mature leaf thickness.*—About 2 mm.

*Mature leaf color.*—Upper side: green RHS 137A. Under side: yellow-green (RHS 146B).

*Leaf base.*—Acute.

*Margin.*—Entire.

*Venation.*—Pattern: parallel. Color of midvein: upper side: green (RHS 137A). under side: yellow-green (RHS 143C).

Raceme:

*Quantity per plant.*—About 1 to 3.

*Number of flowers per raceme.*—About 8 to 14.

*Length.*—About 40 to 50 cm.

*Diameter.*—About 6 cm.

*Strength.*—Strong.

*Aspect.*—Upright.

*Texture.*—Glabrous and smooth.

*Color.*—Green (RHS N137C and RHS 138A).

*Internode.*—Length: about 35 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 mm to 20 mm. Diameter (at midpoint): about 10 mm to 20 mm.

Shape: egg-shaped. Color: yellow-green (RHS 144A) at the base some red-purple (RHS 61A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—Present.

Figure 2:
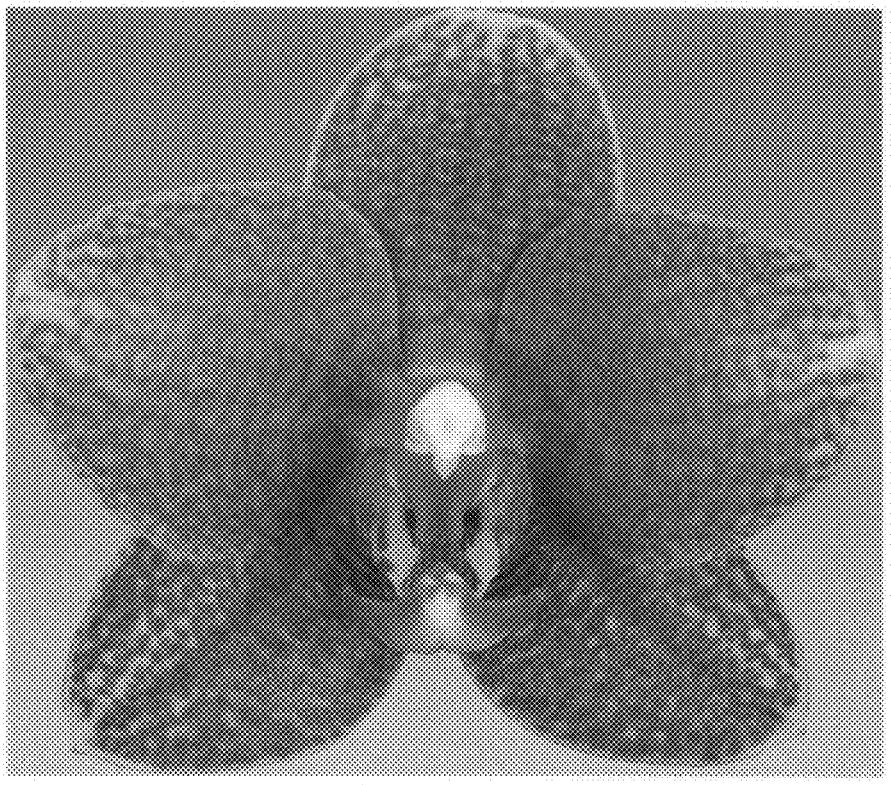
FIG. 2 shows a close-up view of the typical buds and flowers of 'Humming Bird'.
Figure 3:
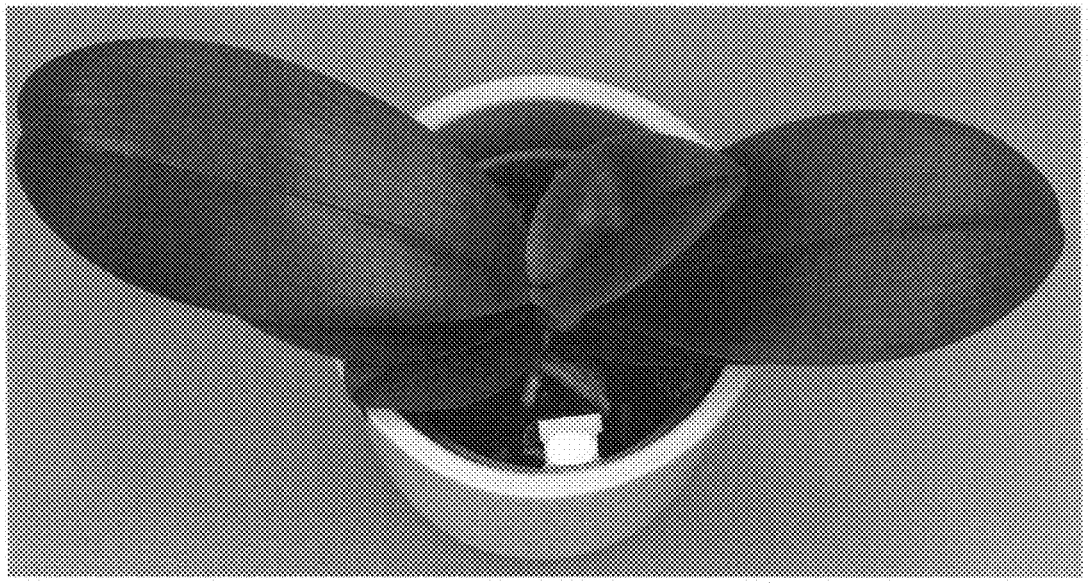
FIG. 3 shows a close-up view of the typical leaves of 'Humming Bird'.

*Flower.*—Rate of opening: Flowers fully opened about 2 to 3 days after petal and sepal separation. Orientation at opening: slanted upward and outward. Shape: Typical shape of *phalaenopsis* orchid; see FIG. 2. Size: Height: about 50 mm. Diameter: about 55 mm. Depth of tube: about 10 mm.

*Petals.*—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: oval. Margin: entire and weakly undulate. Base: broadly ovate. Length: about 25 mm. Width: about 20 mm. Texture: Upper surface: smooth and satiny. Under surface: smooth and satiny. Color (when fully opened): Upper surface: main color is yellow-green (RHS 153D) and is covered with greyed-purple stripes and spots (RHS 185B). In the center some purple-violet (RHS N80A). Under surface: main color is yellow-green (RHS 153D) with some greyed-purple stripes and spots (RHS 185C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: oval. Length: about 15 mm. Width (not flattened): about 13 mm. Texture: Upper and under surface: smooth and satiny. Color (when fully opened): Upper surface: Midlobe: Main color is purple (N79B) with at the base some orange-red (RHS 34B) and at the tip purple (RHS N78A) with two white stripes RHS 155C. Lateral lobes: main color is white (RHS 155C) with purple stripes (RHS N79C) and yellow at the base (RHS 13A). Under surface: Midlobe: purple (RHS N79B) and at the end purple-violet (RHS N80A) with some orange-red (RHS 34A) on the sides. Also some white (RHS 155C) in the center. Lateral lobes: white (RHS 155C) and purple/violet (RHS N80A). Some yellow at the base (RHS 13A). Chirri: about 1 mm. color: white RHS 155C. Pestle (Callosities): Length: about 3 mm. Width (not flattened): about 3 mm. Color: yellow (RHS 13A) with purple spots (RHS N79C). Sides are white (RHS NN155C) and yellow (RHS 13A).

*Pedicel.*—Length: about 30 to 35 mm. Diameter: about 2 mm. Texture: glabrous and smooth. Color: yellow-green (RHS 146D) and close to the flower a light haze of red-purple (RHS 64A).

*Sepals.*—Arrangement: Outer whorl comprises 3 sepals. Overall shape: elliptical and weakly cupped. Margin: entire and weakly undulate. Length: about 27 mm. Width: about 20 mm. Apex: oval; lateral little pointy. Texture: Upper and under surface: smooth and satiny. Color (when fully opened): Upper surface: main color is yellow-green (RHS 153D) covered with greyed-purple stripes and spots (RHS 185B). Under surface: main color is yellow-green (RHS 153D) with some greyed-purple stripes and spots (RHS 185C).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 15 mm. Diameter: about 4 mm. Color: red-purple RHS 73A and white RHS NN155C.

*Pollinia.*—Quantity: Two. Diameter: about 1 mm. Color: yellow-orange RHS 23B.

*Ovary.*—Length: about 5 mm. Diameter: about 6 mm. Color: red-purple RHS 73A and white RHS NN155C.

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Humming Bird', as illustrated and described herein.

* * * * *

UNITED STATES PATENT AND TRADEMARK OFFICE

CERTIFICATE OF CORRECTION

PATENT NO. : PP24,365 P3
APPLICATION NO. : 13/506413
DATED : April 1, 2014
INVENTOR(S) : René Schoone It is certified that error appears in the above-identified patent and that said Letters Patent is hereby corrected as shown below:

ON THE TITLE PAGE, Item (30) insert:

--(30) Foreign Application Priority Data

Apr. 27, 2011 (NL) .....OPS789--

Signed and Sealed this
Twenty-fourth Day of June, 2014

Michelle K. Lee

Michelle K. Lee
*Deputy Director of the United States Patent and Trademark Office*